(12) United States Patent
Kaji et al.

(10) Patent No.: US 10,556,595 B2
(45) Date of Patent: Feb. 11, 2020

(54) STATE ESTIMATION SYSTEM

(71) Applicants: Toyota Jidosha Kabushiki Kaisha, Toyota-shi, Aichi-ken (JP); The University of Tokyo, Bunkyo-ku, Tokyo (JP)

(72) Inventors: Hirotaka Kaji, Hadano (JP); Masashi Sugiyama, Tokyo (JP)

(73) Assignees: Toyota Jidosha Kabushiki Kaisha, Toyota-shi, Aichi-ken (JP); The University of Tokyo, Bunkyo-ku, Tokyo (JP)

( * ) Notice: Subject to any disclaimer, the term of this patent is extended or adjusted under 35 U.S.C. 154(b) by 0 days.

(21) Appl. No.: 16/162,813

(22) Filed: Oct. 17, 2018

(65) Prior Publication Data

US 2019/0126931 A1 May 2, 2019

(30) Foreign Application Priority Data

Oct. 31, 2017 (JP) ................................. 2017-210798

(51) Int. Cl.
*B60W 40/08* (2012.01)
*G06K 9/00* (2006.01)
*G06N 20/00* (2019.01)
*G06K 9/62* (2006.01)

(52) U.S. Cl.
CPC ........... *B60W 40/08* (2013.01); *G06K 9/0055* (2013.01); *G06K 9/00845* (2013.01); *G06K 9/6262* (2013.01); *G06N 20/00* (2019.01); *B60W 2040/0827* (2013.01); *B60W 2540/30* (2013.01); *G06K 2009/00939* (2013.01)

(58) Field of Classification Search
CPC ......... B60W 40/08; B60W 2040/0827; B60W 2450/30; G06N 20/00; G06K 9/00845
USPC ....................................... 340/576, 573.1, 3.1
See application file for complete search history.

(56) References Cited

U.S. PATENT DOCUMENTS

2017/0112451 A1* 4/2017 Meyerson ............ A61B 5/0205

FOREIGN PATENT DOCUMENTS

JP 2015-226696 A 12/2015

* cited by examiner

*Primary Examiner* — Daryl C Pope
(74) *Attorney, Agent, or Firm* — Dinsmore & Shohl LLP

(57) ABSTRACT

A state estimation system includes a processor configured to: obtain first input data related to a first user; obtain second input data related to a second user; perform an estimation operation for estimating a state of the first user and a training operation for optimizing a content of the estimation operation by using i) first training data which includes the first input data and the first label data associated with each other, ii) second training data which includes the first input data so as not to associate the first input data and the first label data with each other, and iii) third training data which includes the second input data and the second label data associated with each other; and output information related to the content of the estimation operation.

8 Claims, 5 Drawing Sheets

STATE ESTIMATION SYSTEM

CROSS-REFERENCE TO RELATED APPLICATIONS

This application claims priority to Japanese Patent Application No. 2017-210798 filed on Oct. 31, 2017, which is incorporated herein by reference in its entirety including the specification, drawings and abstract.

BACKGROUND

1. Technical Field

The disclosure relates to a state estimation system.

2. Description of Related Art

As an example of a method for estimating a state of a user, Japanese Unexamined Patent Application Publication No. 2015-226696 (JP 2015-226696 A) describes a sleepiness detection method of obtaining a feature value of an electrocardiogram waveform when a driver is awake, constructing a sleepiness detection model for each driver based on standardized data when the driver is awake, and detecting the sleepiness of a driver based on the constructed sleepiness detection model.

SUMMARY

The method described in JP 2015-226696 A constructs the sleepiness detection model for each driver based on the feature value of the electrocardiogram waveform obtained immediately after the driver starts to drive the vehicle (specifically, within about three minutes after the driver starts to drive the vehicle). However, since the sleepiness detection model is constructed after the driver starts to drive the vehicle, there is an interval at which the sleepiness detection model is not able to be constructed for a while after the driver starts to drive the vehicle. Since the feature value of the electrocardiogram waveform has large individual differences or intra-individual differences and there is also a problem of artifact due to the operation, an appropriate sleepiness detection model may not be constructed based on solely the feature value of the electrocardiogram waveform of the driver for three minutes. As a result, according to the method described in JP 2015-226696 A, there is a possibility that the sleepiness of the driver is not likely to be appropriately detected.

The possibility described above is not limited to the case where the sleepiness of the driver is detected based on the feature value of the electrocardiogram waveform of the driver, and may similarity occur even when the state of the user is estimated based on at least one of any biological information of the user and any behavior information of the user.

The disclosure provides a state estimation system capable of appropriately estimating a state of a user based on at least one of biological information and behavior information of the user.

A state estimation system according to an aspect of the disclosure includes a processor configured to: obtain first input data related to at least one of biological information and behavior information of a first user; obtain second input data related to at least one of biological information and behavior information of a second user different from the first user; perform an estimation operation for estimating a state of the first user based on the first input data; perform a training operation for optimizing a content of the estimation operation by using i) first training data which includes the first input data and first label data indicating a state of the first user corresponding to the first input data so as to associate the first input data and the first label data with each other, ii) second training data which includes the first input data so as not to associate the first input data and the first label data with each other, and iii) third training data which includes the second input data and second label data indicating a state of the second user corresponding to the second input data so as to associate the second input data and the second label data with each other; and output a signal indicating information related to the content of the estimation operation.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Hereinafter, an embodiment of a state estimation system will be described. Hereinafter, a state estimation system 1 capable of estimating a degree of sleepiness of a driver based on an electrocardiographic waveform of the driver of a vehicle is described as the embodiment of the state estimation system of the disclosure. The driver is a specific example of a "first user" according to the aspect of the disclosure.

(1) Configuration of State Estimation System 1

Figure 1:
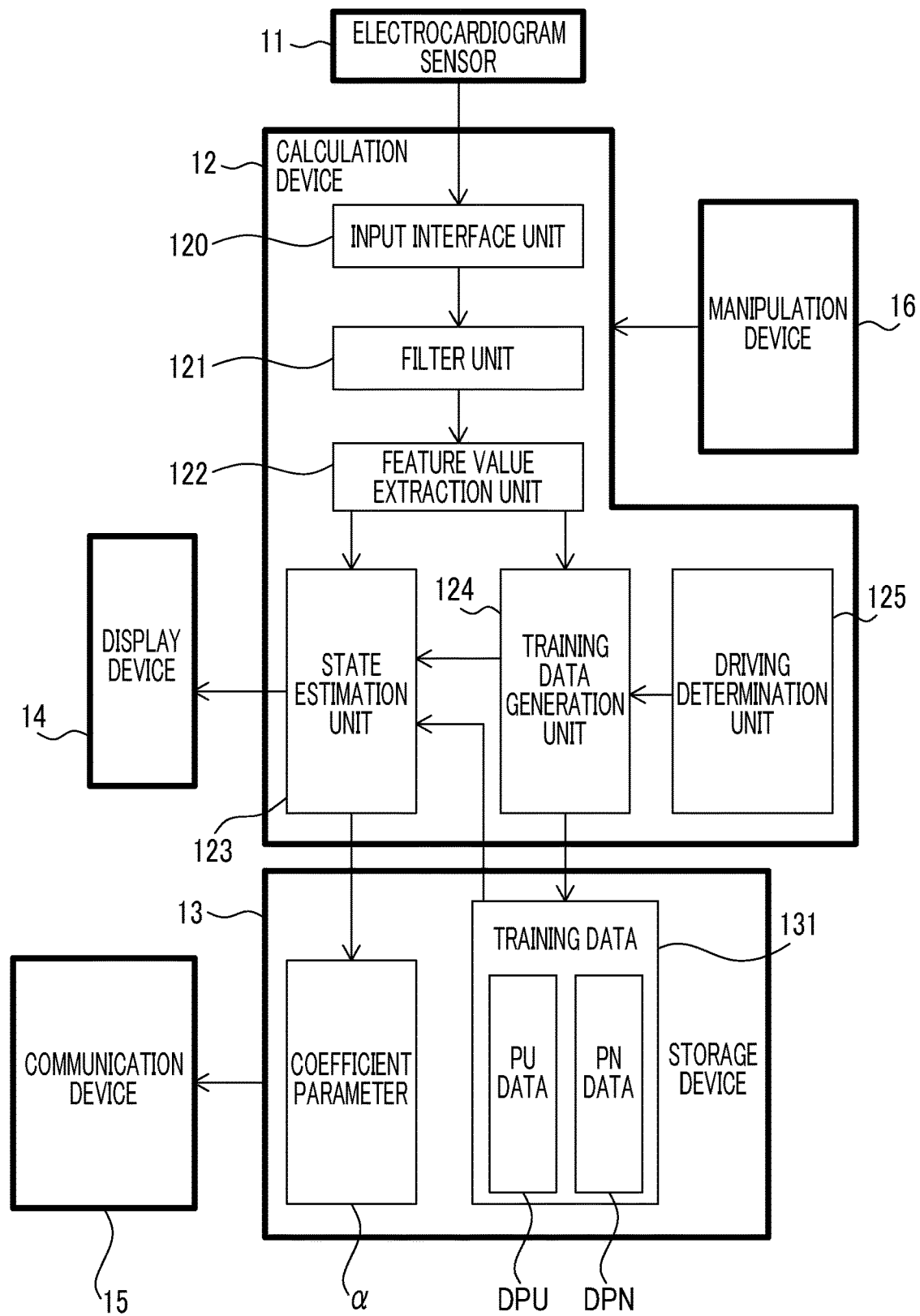
FIG. 1 is a block diagram showing a configuration of a state estimation system according to the present embodiment.

Initially, the configuration of the state estimation system 1 according to the present embodiment will be described with reference to FIG. 1. FIG. 1 is a block diagram showing the configuration of the state estimation system 1 according to the present embodiment.

As shown in FIG. 1, the state estimation system 1 includes a electrocardiogram sensor 11, a calculation device 12, a storage device 13, a display device 14, a communication device 15, and a manipulation device 16.

The electrocardiogram sensor 11 is an electrocardiography device capable of detecting electrocardiogram (that is, an electric signal produced by the heart) of the driver. A method of detecting the electrocardiogram using the electrocardiogram sensor 11 may be any method. For example, the electrocardiogram sensor 11 may be a wearable sensor that is detachably attached to the chest of the driver or may be fixed to the vehicle. The detection result (that is, a waveform signal indicating a time waveform of the electrocardiogram) of the electrocardiogram sensor 11 is output to the calculation device 12.

The calculation device 12 is an information processing device such as a central processing unit (CPU). The calculation device 12 estimates the degree of sleepiness of the driver based on a waveform signal output from the electrocardiogram sensor 11. Specifically, the calculation device 12 estimates whether or not the driver is in a sleepy state or an unsleepy state (that is, an awake state). In order to estimate the degree of sleepiness, the calculation device 12 includes, as a processing block logically constructed within the calculation device 12, an input interface unit 120 which is a specific example of an "obtainment unit" according to the aspect of the disclosure, a filter unit 121, a feature value extraction unit 122, a state estimation unit 123 which is a specific example of an "estimation unit" according to the aspect of the disclosure, a training data generation unit 124, and a driving determination unit 125. The input interface unit 120 obtains the waveform signal output from the electrocardiogram sensor 11. The filter unit 121 filters the waveform signal obtained by the input interface unit 120. The feature value extraction unit 122 extracts a feature value of the filtered waveform signal. The state estimation unit 123 performs an estimation operation for estimating the degree of sleepiness of the driver based on the feature value extracted by the feature value extraction unit 122. The state estimation unit 123 performs a training operation for optimizing a coefficient parameter $\alpha$ (the details thereof will be described below) that defines the content of the estimation operation. The training data generation unit 124 generates training data items DP to be used when the state estimation unit 123 performs the training operation based on the feature value extracted by the feature value extraction unit 122. The training data items DP include two kinds of data items such as PU data DPU and PN data DPN. The details of the PU data DPU and the PN data DPN will be described below. The driving determination unit 125 determines whether or not the driver drives the vehicle.

The storage device 13 is a hard disk or a recording medium such as a flash memory. The storage device 13 stores any data related to the operation of the state estimation system 1. Particularly, the storage device 13 stores the coefficient parameter $\alpha$ optimized through the training operation and the training data items DP to be used in the training operation. In addition, the storage device 13 may store data indicating the degree of sleepiness estimated through the estimation operation, data indicating the waveform signal, or data indicating the extracted feature value. The state estimation system 1 may include an external storage device capable of transmitting and receiving data to and from the state estimation system 1 via the communication device 15 in addition to or instead of the storage device 13.

The display device 14 performs any display operation related to the operation of the state estimation system 1. For example, the display device 14 displays the estimation result of the degree of sleepiness of the driver using the calculation device 12.

The communication device 15 controls the transmission and reception of the data between the state estimation system 1 and an external device. For example, the communication device 15 controls the transmission and reception of the data stored in the storage device 13 between the state estimation system 1 and the external device.

The manipulation device 16 receives a manipulation input of the driver (or any user who uses the state estimation system 1) related to the operation of the state estimation system 1. For example, the manipulation device 16 receives a manipulation input for requesting the starting and ending of the estimation operation.

The state estimation system 1 includes a mobile terminal (for example, a smartphone) that includes the calculation device 12, the storage device 13, the display device 14, the communication device 15, and the manipulation device 16. In this case, the degree of sleepiness of the driver who drives the vehicle is estimated as long as the driver rides the vehicle while holding the mobile terminal. Here, the state estimation system 1 may not include such a mobile terminal as long as the state estimation system includes the calculation device 12, the storage device 13, the display device 14, the communication device 15, and the manipulation device 16.

(2) Operation of State Estimation System 1

The operation of the state estimation system 1 will be described. As stated above, the state estimation system 1 performs the estimation operation for estimating the degree of sleepiness of the driver and the training operation for optimizing the coefficient parameter $\alpha$. Accordingly, hereinafter, the estimation operation and the training operation will be described in order.

(2-1) Estimation Operation

Figure 2:
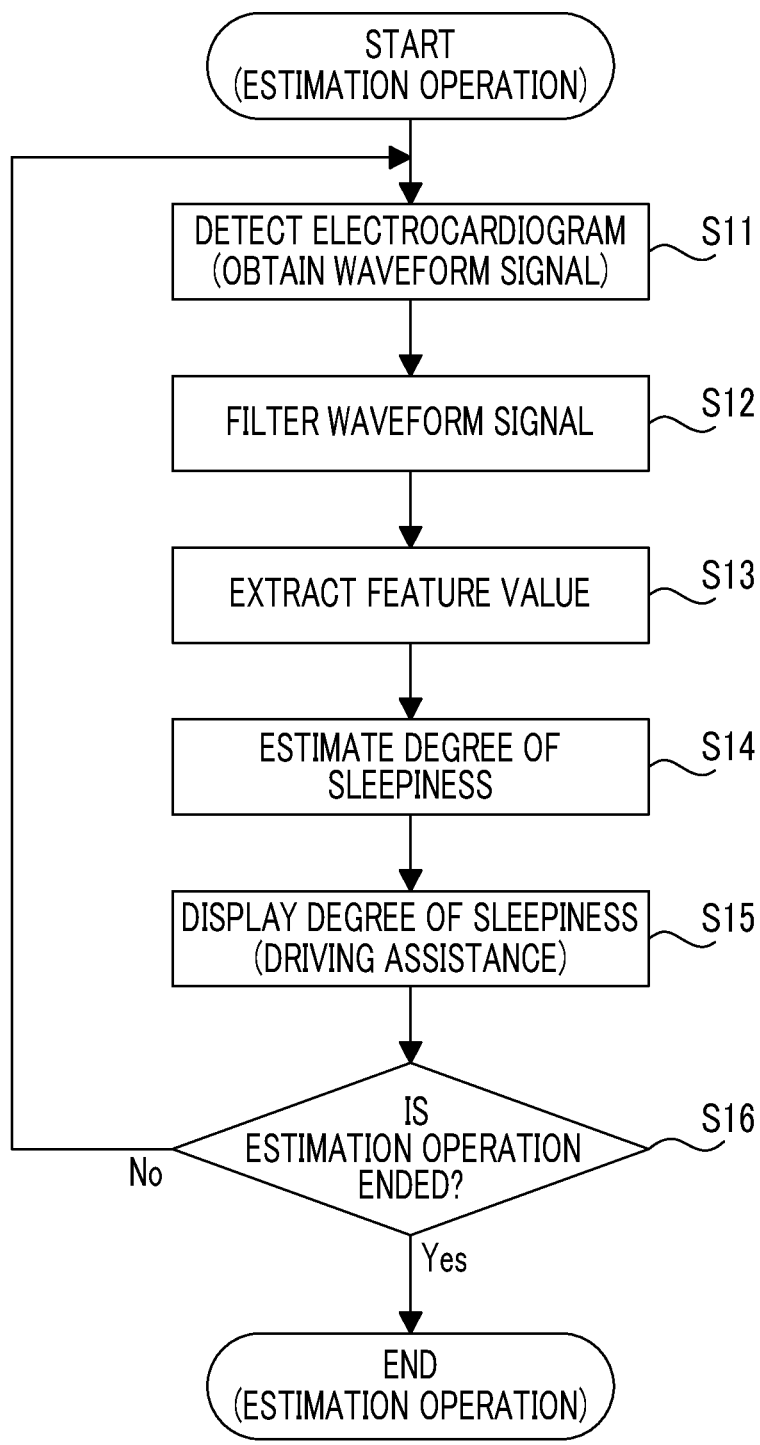
FIG. 2 is a flowchart showing a flow of an estimation operation.

Initially, the estimation operation will be described with reference to FIG. 2. FIG. 2 is a flowchart showing a flow of the estimation operation.

As shown in FIG. 2, when the driver requests the starting of the estimation operation by using the manipulation device 16, the electrocardiogram is detected by the electrocardiogram sensor 11 (step S11). As a result, the input interface unit 120 obtains the waveform signal indicating the electrocardiogram (step S11).

Thereafter, the filter unit 121 filters the waveform signal obtained in step S11 (step S12). The filtering may include first processing for removing noise from the waveform signal. The filtering may include second processing for removing oscillation (that is, fluctuation) in a baseline of the waveform signal.

Figure 3:
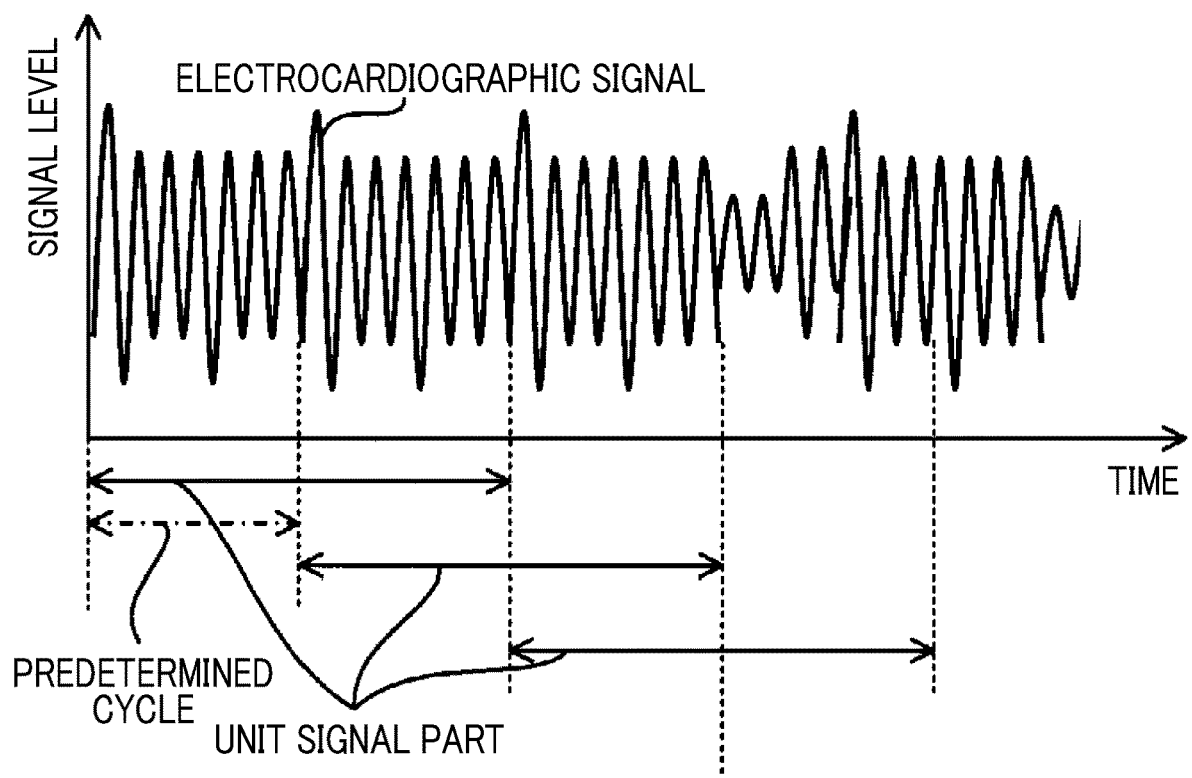
FIG. 3 is a graph showing a waveform signal of electrocardiogram.

Subsequently, the feature value extraction unit 122 extracts the feature value of the filtered waveform signal (step S13). Specifically, the feature value extraction unit 122 sectionalizes the waveform signal as unit signal parts each having a predetermined time length (for example, several tens of seconds to hundreds of seconds) as shown in FIG. 3. The feature value extraction unit 122 extracts a feature value of the unit signal part. The feature value extraction unit 122 repeats processing for extracting the feature value of the unit signal part for every predetermined cycle (for example, several tens of seconds to hundreds of seconds). FIG. 3 shows an example in which the predetermined cycle is shorter than the time length of the unit signal part. In this case, one unit signal part and another unit signal part partially overlap each other.

Figure 4:
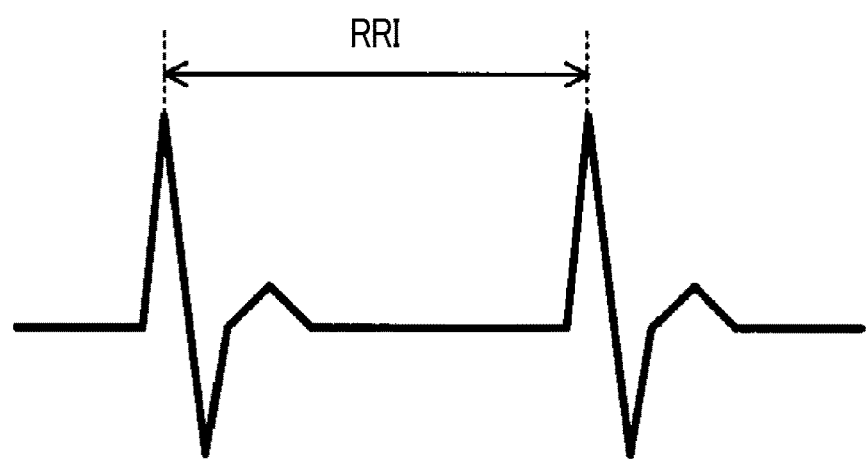
FIG. 4 is a waveform diagram showing an R-R-interval (RRI) capable of being specified from the waveform signal.

The feature value is a parameter indicating a feature of the waveform signal. It will be described in the present embodiment that the feature value extraction unit 122 extracts a feature value related to RRI, another feature value may be extracted. As shown in FIG. 4, the RRI is an index corresponding to a time interval of a peak of an R wave. For example, the feature value related to the RRI includes at least one of LF corresponding to the strength of a low frequency component (for example, a signal component corresponding to a frequency ranging from 0.04 Hz to 0.15 Hz) detected when fast Fourier transform (FFT) is performed on the RRI, HF corresponding to the strength of a high frequency component (for example, a signal component corresponding to a frequency ranging from 0.15 Hz to 0.40 Hz) detected when the FFT is performed on the RRI, pNN50 corresponding to the proportion of heartbeats (or the number of heartbeats) in which a difference between two adjacent RRIs on a time axis exceeds 50 milliseconds, RMSSD corresponding to a square root of an average value of squared values of a difference between two adjacent RRIs on a time axis, SD/RMSSD corresponding to a value obtained by dividing a standard deviation of the RRIs by the RMSSD, a variance value of the RRIs, and the number of R waves (that is, the number of peaks of the waveform).

Here, there is a possibility that the feature value extraction unit 122 will not appropriately extract the feature value in some states of the waveform signal. In this case, the feature value extraction unit 122 may output an error flag indicating that it is not possible to appropriately extract the feature value. For example, there is a possibility that a feature value extracted from a waveform signal of which a signal level (that is, amplitude) is too small (for example, a waveform signal which is lower than a predetermined level) will have relatively low reliability. Accordingly, when the signal level of the waveform signal is too small, the feature value extraction unit 122 may output the error flag. When the error flag is output, the state estimation unit 123 may not estimate the degree of sleepiness of the driver.

The feature value (additionally, the error flag) extracted by the feature value extraction unit 122 is output to the state estimation unit 123 from the feature value extraction unit 122. The feature value (additionally, the error flag) extracted by the feature value extraction unit 122 is stored by the storage device 13. At this time, as will be described below, the storage device 13 may store the feature value extracted by the feature value extraction unit 122, as a part of the training data items DP. The feature value extracted by the feature value extraction unit 122 in step S13 is a specific example of "first input data" according to the aspect of the disclosure.

Referring back to FIG. 2, the state estimation unit 123 subsequently estimates the degree of sleepiness of the driver based on the feature value extracted in step S13 (step S14). Specifically, the state estimation unit 123 initially calculates a basis vector $\varphi(x)$ expressed in Expression 1 based on the PU data DPU and the PN data DPN stored in the storage device 13. In Expression 1, when a variable x is the feature value (particularly, the feature value of a certain unit signal part) extracted in step S13 and the number of kinds of the extracted feature values is d, a d-dimensional vector (that is, a matrix) is obtained as expressed in Expression 2. In Expression 1, a variable b is the dimension of the basis vector $\varphi(x)$. Subsequently, the state estimation unit 123 reads out the coefficient parameter $\alpha$ stored in the storage device 13. The coefficient parameter $\alpha$ is a b-dimensional vector, and is expressed in Expression 3. Thereafter, the state estimation unit 123 estimates the degree of sleepiness based on a linear model $g(x)$ defined by the basis vector $\varphi(x)$ and the coefficient parameter $\alpha$. The linear model $g(x)$ is expressed in Expression 4. Specifically, the state estimation unit 123 inputs the feature value x extracted in step S13 to the linear model $g(x)$, and obtains an output value of the linear model $g(x)$. The linear model $g(x)$ outputs an output value corresponding to the degree of sleepiness of the driver which is estimated from the feature value x. In the following description, it is assumed that the higher the degree of sleepiness of the driver (that is, the higher a possibility that the driver will be sleepy), the smaller the output value output by the linear model $g(x)$ in a range of $-1$ to $+1$. Here, the optimization of the coefficient parameter $\alpha$ through the training operation to be described below, the coefficient parameter is optimized such that the linear model $g(x)$ outputs $-1$ (or a value close to $-1$) when the degree of sleepiness of the driver is relatively high (that is, a possibility that the driver will be sleepy is relatively high), and outputs $+1$ (or a value close to $+1$) when the degree of sleepiness of the driver is relatively low (that is, a possibility that the driver will be sleepy is relatively low). Subsequently, when the output value of the linear model $g(x)$ is larger than a predetermined threshold (for example, 0), the state estimation unit 123 estimates that the driver is unsleepy. Meanwhile, when the output value of the linear model $g(x)$ is smaller than the predetermined threshold (for example, 0), the state estimation unit 123 estimates that the driver will be sleepy. Accordingly, the state estimation unit 123 is substantially equivalent to a two-class classifier.

$$\varphi(x)=(\varphi_1(x),\varphi_2(x),\ldots,\varphi_b(x))^T \qquad \text{[Expression 1]}$$

$$x=(x1,x2,\ldots,xd)\in R^d \qquad \text{[Expression 2]}$$

$$\alpha=(\alpha_1,\alpha_2,\ldots,\alpha_b)^T \qquad \text{[Expression 3]}$$

$$g(x)=\alpha^T\varphi(x) \qquad \text{[Expression 4]}$$

Thereafter, the display device 14 displays the estimation result of the degree of sleepiness of the driver in step S14 (step S15). When the state estimation unit estimates that the driver is sleepy, the calculation device 12 may warn the driver as needed. For example, the calculation device 12 may control the display device 14 to display a warning image for warning the driver. For example, the calculation device 12 may control a speaker (not shown) to output a warning sound for warning the driver. For example, the calculation device 12 may control a vibration device (not shown) built in a seat or a steering wheel of the vehicle to generate vibration for warning the driver.

The processes of steps S11 to S15 described above are repeatedly performed until the driver requests the ending of the estimation operation by using the manipulation device 16 (step S16).

(2-2) Training Operation

The training operation will be described. In the present embodiment, the state estimation system 1 performs the training operation before the state estimation system 1 starts the estimation operation. The state estimation system 1 performs the training operation even after the state estimation system 1 starts the estimation operation. Accordingly, the training operation (hereinafter, referred to as an "initial training operation") performed before the state estimation system 1 starts the estimation operation and the training operation (hereinafter, referred to as a "continuous training operation") performed after the state estimation system 1 starts the estimation operation will be described in order.

(2-2-1) Initial Training Operation

The state estimation system 1 performs the initial training operation before the state estimation system 1 is obtained by the driver (in other words, before the state estimation system 1 is shipped to the market). In other words, the state estimation system 1 performs the initial training operation before the state estimation system 1 estimates the degree of sleepiness of the driver. At this stage, it is difficult for the state estimation system 1 to perform the initial training operation by using the detection result of the electrocardiogram of the driver as an estimating target of the degree of sleepiness using the state estimation system 1. Thus, the state estimation system 1 performs the initial training operation by using the detection result of the electrocardiogram of a subject different from the driver.

Specifically, the electrocardiogram of the subject (typically, a subject different from the driver) who cooperates in the initial training operation is detected by the electrocardiogram sensor 11. The subject is a specific example of a "second user" according to the aspect of the disclosure. Thereafter, the feature value extraction unit 122 extracts the feature value based on the detection result of the electrocardiogram of the subject. The extracted feature value is output to the training data generation unit 124 from the feature value extraction unit 122. The feature value extracted in the initial training operation is a specific example of "second input data" according to the aspect of the disclosure.

The detection of the electrocardiogram and the extraction of the feature values are performed in parallel, and the subject is captured by a camera (not shown). Thereafter, a annotator (for example, an expert such as a doctor) specifies at least one of the facial expression and action of the subject from the captured result using the camera, and determines whether the subject is sleepy or unsleepy based on the at least one of the specified facial expression and action. That is, the annotator determines an actual degree of sleepiness of the subject at a point of time when the electrocardiogram is detected and the feature values are extracted. For example, the determination result by the annotator is input to the training data generation unit 124 by using the manipulation device 16. The determination result by the annotator is a specific example of "second label data" according to the aspect of the disclosure.

The extraction of the feature value of the electrocardiogram of the subject and the determination of the actual degree of sleepiness of the subject are repeatedly performed for a plurality of subjects. As a result, the feature values of the electrocardiogram of the subjects and the actual degrees of sleepiness of the subjects are input to the training data generation unit 124. The training data generation unit 124 generates data which includes the extracted feature values and the determination results (that is, label data items indicating labels of the degrees of sleepiness of the subjects) by the annotator such that the extracted feature value and the determination results are associated with the respective subjects, as the PN data items DPN which are a part of the training data items DP. The generated PN data items DPN are stored in the storage device 13. Since there are the subjects, there is a high possibility that the PN data items DPN will include both data obtained by associating a feature value of electrocardiogram of a first subject who is sleepy with label data indicating that the first subject is sleepy at a point of time when the electrocardiogram is detected and data obtained by associating a feature value of electrocardiogram of a second subject (here, the second subject is different from the first subject) who is unsleepy with label data indicating that the second subject is unsleepy at a point of time when the electrocardiogram is detected. When the detection of the electrocardiogram of the subject is continuously performed to some extent, there is a possibility that the state of the subject is changed from the sleepy state to the unsleepy state or from the unsleepy state to the sleepy state during the detection of the electrocardiogram. As a result, there is a high possibility that the PN data DPN will include both data obtained by associating the feature value of the electrocardiogram of the first subject who is sleepy in a first timing with label data indicating that the first subject is sleepy in the first timing and data obtained by associating the feature value of the electrocardiogram of the first subject who is unsleepy in a second timing different from the first timing with label data indicating that the first subject is unsleepy in the second timing. That is, in order to optimize the content of the estimation operation for classifying the state of the subject into two classes such as the sleepy state (for example, a negative state) and the unsleepy state (for example, a positive state) (that is, in order to optimize the coefficient parameter $\alpha$), the PN data DPN includes both data (so-called positive data) obtained by associating label data indicating the subject is in the positive state with the feature value and data (so-called negative data) obtained by associating label data indicating that the subject is in the negative state with the feature value. The PN data DPN is a specific example of "third training data" according to the aspect of the disclosure.

Subsequently, the state estimation unit 123 optimizes the coefficient parameter $\alpha$ that defines the content of the estimation operation by using the PN data DPN. In this case, since the PN data DPN includes the label data (so-called training data) indicating the actual degree of sleepiness of the subject as stated above, the state estimation unit 123 optimizes the coefficient parameter $\alpha$ based on a supervised learning method. Specifically, the state estimation unit 123 optimizes the coefficient parameter $\alpha$ such that an error (that is, a loss, for example, a squared loss) between the output value output from the linear model $g(x)$ when the feature value x included in the PN data DPN is input to the linear model $g(x)$ expressed in Expression 4 and the label data included in the PN data DPN is minimized or is equal to or smaller than a first allowable value. As a result, the content of the estimation operation is optimized. The optimized coefficient parameter $\alpha$ is stored in the storage device 13.

(2-2-2) Continuous Training Operation

Figure 5:
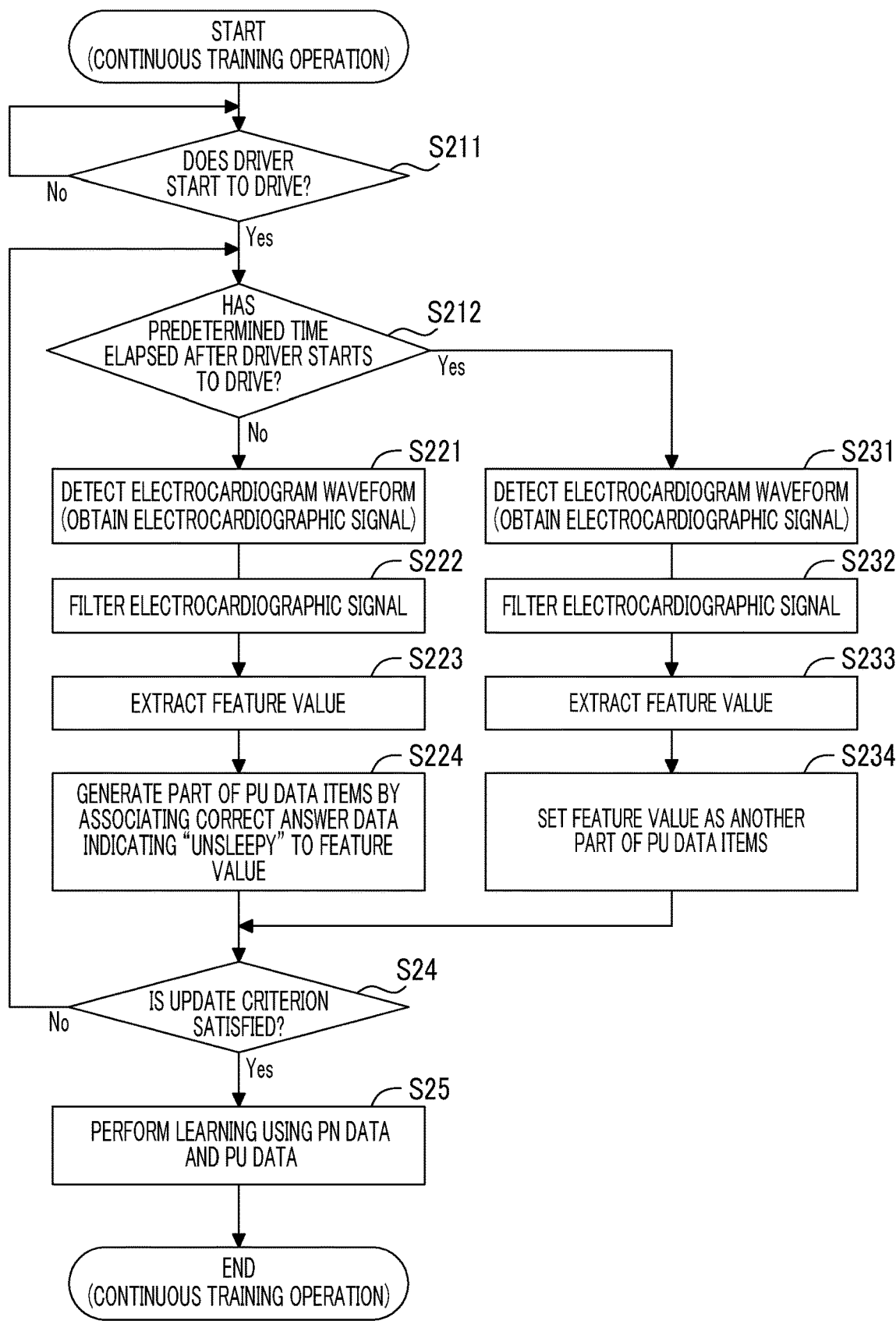
FIG. 5 is a flowchart showing a flow of a continuous training operation.

After the state estimation system 1 is obtained by the driver (in other words, the state estimation system 1 is shipped to the market), the state estimation system 1 performs the continuous training operation. In other words, after the state estimation system 1 starts to estimate the degree of sleepiness of the driver, the state estimation system 1 performs the continuous training operation. At this stage, since the driver drives the vehicle, the state estimation system 1 can perform the continuous training operation by using the detection result of the electrocardiogram of the driver as the estimating target of the degree of sleepiness using the state estimation system 1. The storage device 13 stores the PN data items DPN related to the detection results of the electrocardiogram of the subjects different from the driver which are used in the initial training operation. Thus, the state estimation system 1 can perform the continuous training operation by using even the PN data items DPN. Hereinafter, the continuous training operation will be described with reference to FIG. 5. FIG. 5 is a flowchart showing a flow of the continuous training operation. The continuous training operation is typically performed in parallel with the aforementioned estimation operation, but may be performed for a period of time during which the estimation operation is not performed.

As shown in FIG. 5, the PU data DPU which is the training data DP is initially obtained based on the detection result of the electrocardiogram of the driver. Specifically, the driving determination unit 125 initially determines whether or not the driver drives the vehicle (step S211). For example, when the driver holds the mobile terminal including the calculation device 12 as stated above, the driving detection unit 125 may estimate the behavior of the driver based on the detection result of an acceleration sensor (not shown) included in the mobile terminal, and may determine that the driver drives the vehicle when the driving detection unit estimates that the driver rides the vehicle. Alternatively, the driving detection unit 125 may estimate a degree of proximity of the communication device 15 included in the mobile terminal to the communication device 15 included in the vehicle from a reception signal of the communication device 15 included in the mobile terminal, and may determine that the driver drives the vehicle when the driving detection unit estimates that the communication device 15 included in the mobile terminal and the communication device included in the vehicle approach each other as the driver is deemed to ride the vehicle. Alternatively, when the state estimation system 1 is installed on the vehicle, the driving detection unit 125 may determine whether or not the driver drives the vehicle based on a state of the vehicle (for example, a state of an ignition switch).

When the driving detection unit determines that the driver does not drive the vehicle as the determination result in step S211 (step S211: No), the driving detection unit 125 continues to determine whether or not the driver drives the vehicle.

Meanwhile, when the driving detection unit determines that the driver drives the vehicle as the determination result in step S211 (step S211: Yes), the driving detection unit 125 determines whether or not a predetermined time (for example, few minutes) has elapsed after the driver starts to drive the vehicle (step S212).

When the driving detection unit 125 determines that the predetermined time has not elapsed yet after the driver starts to drive the vehicle as the determination result in step S212 (step S212: No), the driving detection unit estimates that the driver just starts to drive the vehicle. In this case, there is a relatively high possibility that the driver will be unsleepy. This is because since the driver easily feels sleepy when the vehicle aimlessly continues to drive the vehicle, the driver has not been driving the vehicle for such a long period of time at this stage. Thus, there is a high possibility that the feature value of the electrocardiogram detected in this case will correspond to the feature value of the electrocardiogram of the driver who is unsleepy. That is, when the electrocardiogram of the driver is detected in this timing, there is a high possibility that the feature value of the electrocardiogram of the driver who is unsleepy is extracted. In the present embodiment, the electrocardiogram of the driver is detected by the electrocardiogram sensor 11 (step S221), the waveform signal is filtered by the filter unit 121 (step S222), and the feature value of the waveform signal is extracted by the feature value extraction unit 122 (step S223). The processing in steps S221 to S223 may be the same as the processing in steps S11 to S13. The extracted feature value is output to the training data generation unit 124 from the feature value extraction unit 122. Thereafter, the training data generation unit 124 generates data obtained by associating the extracted feature value with the label data indicating the label representing that the state of the subject is unsleepy, as a part of the PU data items DPU (step S224). That is, the training data generation unit 124 generates the data (so-called positive data) including the label data indicating that the subject is in the positive state, as a part of the training data items DP (more specifically, a part of the PU data items DPU). The generated PU data DPU is stored in the storage device 13. The feature value extracted in step S223 is a specific example of "first input data" according to the aspect of the disclosure. The label data associated with the feature value in step S224 is a specific example of "first label data" according to the aspect of the disclosure. The PU data DPU created in step S224 is a specific example of "first training data" according to the aspect of the disclosure.

Meanwhile, when the driving detection unit determines that the predetermined time has already elapsed after the driver starts to drive the vehicle as the determination result in step S212 (step S212: Yes), the driver may be unsleepy or may be sleepy. That is, there is a high possibility that the degree of sleepiness of the driver will be changed due to the influence of various causes. In other words, the degree of sleepiness of the driver is indeterminate. Even in this case, in the present embodiment, the electrocardiogram of the driver is detected by the electrocardiogram sensor 11 (step S231), the waveform signal is filtered by the filter unit 121 (step S232), and the feature value of the waveform signal is extracted by the feature value extraction unit 122 (step S233). The processing in steps S231 to S233 may be the same as the processing in steps S11 to S13. The extracted feature value is output to the training data generation unit 124 from the feature value extraction unit 122. The feature value extracted in this case may correspond to the feature value of the electrocardiogram of the driver who unsleepy or may correspond to the feature value of the electrocardiogram of the driver who is sleepy. The training data generation unit 124 sets the extracted feature value as a part of the PU data items DPU without associating the extracted feature value with the label data indicating the actual degree of sleepiness of the subject (step S234). That is, the training data generation unit 124 may generate data (so-called unlabeled data) which does not include information related to the degree of sleepiness of the subject, as a part of the training data items DP (more specifically, a part of the PU data items DPU). The generated PU data DPU is stored in the storage device 13. The feature value extracted in step S233 is a specific example of "first input data" according to the aspect of the disclosure. The PU data DPU created in step S234 is a specific example of "second training data" according to the aspect of the disclosure.

As stated above, the predetermined time used in step S212 is used to distinguish between a state in which the driver drives the vehicle in the unsleepy state and a state in which the degree of sleepiness of the driver is indeterminate based on a time elapsing after the driver starts to drive the vehicle. Accordingly, the predetermined time is set as an appropriate value with which these two states are able to be appropriately distinguished.

Subsequently, the training data generation unit 124 determines whether or not an update criterion is satisfied (step S24). The update criterion indicates a condition to be satisfied in order to start the optimization of the coefficient parameter α using the PU data DPU and the PN data DPN. For example, the update criterion is a condition in which the data amount of PU data items DPU which are newly generated after the previous coefficient parameter α is optimized is equal to or larger than a predetermined amount. The larger the predetermined amount, the smaller the number of times the coefficient parameter α is optimized. Thus, the predetermined amount is set as an appropriate value such that the coefficient parameter α is optimized with the appropriate number of times.

When the training data generation unit determines that the update criterion has not been satisfied yet as the determination result in step S24 (step S24: No), the operation subsequent to step S212 is repeated. That is, the PU data DPU which is a part of the training data DP continues to be generated.

When the training data generation unit determines that the update criterion is satisfied as the determination result in step S24 (step S24: Yes), the state estimation unit 123 optimizes the coefficient parameter α by using the PU data DPU and the PN data DPN stored in the storage device 13 (step S25).

The optimization of the coefficient parameter α using the PN data DPN corresponds to training based on the supervised learning method as stated above. Meanwhile, as stated above, the PU data DPU includes the feature value (that is, positive data) associated with the label data indicating that the driver is unsleepy and the feature value (that is, unlabeled data) which is not associated with the label data. Thus, the optimization of the coefficient parameter α using the PU data DPU may be performed based on a PU learning method (PU classification).

As stated above, the PN data items DPN include subject data items obtained by associating the feature values with the label data items as much as the number of subjects. Thus, the optimization of the coefficient parameters a using the PN data items DPN is constituted by a plurality of tasks for optimizing the coefficient parameters a based on a plurality of subject data items which respectively corresponds to the subjects. Hereinafter, the tasks constituting the optimization of the coefficient parameters a using the PN data items DPN are referred to as "PN tasks" for the sake of convenience in description. The coefficient parameters a to be optimized by using the PU data items DPU are the same as the coefficient parameters a to be optimized by using the PN data DPN. Thus, the tasks (hereinafter, the tasks constituting the optimization of the coefficient parameters a using the PU data items DPU are referred to as "PU tasks" for the sake of convenience in description) constituting the optimization of the coefficient parameters a using the PU data items DPU and the PN tasks constituting the optimization of the coefficient parameters a using the PN data items DPN are the tasks related to each other. In this case, the state estimation unit 123 may perform the PN tasks and the PU tasks based on a multi-task learning method in order to improve training precision, but not particularly limited thereto.

Hereinafter, an example of the training operation of step S25 which performs the PN tasks and the PU tasks based on the multi-task learning method will be described. Initially, unit data (that is, a combination of a certain feature value x with label data y) constituting the PN data items DPN and the PU data items DPU (here, exception for the unlabeled data) is expressed in Expression 5. In Expression 5, a variable i is an identification number of the unit data. The label data y corresponds to a class label which is any of +1 and −1 as expressed in Expression 6. A unique task number t is assigned to each of the PN tasks and the PU tasks. The task number t is expressed in Expression 7. In Expression 7, T is the number of PN tasks and PU tasks. A basis function $\varphi_t(x)$ corresponding to a task having a task number t, a coefficient parameter $\alpha_t$, and a linear model $g_t(x)$ are respectively expressed in Expressions 8 to 10.

$(x_i, y_i)$ [Expression 5]

$y \in \{-1, +1\}$ [Expression 6]

$t \in \{1, 2, \ldots, T\}$ [Expression 7]

$\varphi_t(x) = (\varphi_{t1}(x), \varphi_{t2}(x), \ldots, \varphi_{tb}(x))^T$ [Expression 8]

$\alpha_t = (\alpha_{t1}, \alpha_{t2}, \ldots, \alpha_{tb})^T$ [Expression 9]

$g_t(x) = \alpha_t^T \varphi_t(x)$ [Expression 10]

A learning criterion for optimizing the coefficient parameter α is set for the linear model g(x) defined in this manner.

Specifically, a learning criterion shown in Expression 12 is able to be set when a squared loss $l_s(z)$ shown in Expression 11 is adopted, for example. In Expression 11, a variable z is the product of the label data y and the output of the linear model g(x) to which the feature value x associated with the label data y is input. A first term in Expression 12 is a term corresponding to a loss of the PU task. A second term in Expression 12 is a term corresponding to a loss of the PN task. A third term in Expression 12 corresponds to a regularization term. A fourth term in Expression 12 corresponds to an information sharing term between the tasks. In a variable N in Expression 12 is the total number of positive data items and unlabeled data items included in the PU data DPU. In a variable M in Expression 12 is the number of unit data items included in the PN data DPN (that is, the total number of positive data items and negative data items). A variable L in Expression 12 is the sum of the variable N and the variable M. A variable $\lambda_t$ in Expression 12 is a hyper parameter corresponding to a task having a task number t. A variable w in Expression 12 is a hyper parameter. Variables t, t' in Expression 12 are respectively task numbers. Variable $\gamma_{t,t'}$ in Expression 12 is a hyper parameter corresponding to a combination of the task having the task number t and a task having a task number t'.

$l_s(z) = \frac{1}{4}(z-1)^2$ [Expression 11]

$\hat{J}_S(\alpha) = \frac{N}{L} J_S^{\hat{P}U}(\alpha) + \frac{M}{L} J_S^{\hat{P}N}(\alpha) +$ [Expression 12]

$\frac{1}{2}\sum_{t=1}^{T} \lambda_t \alpha_t^T \alpha_t + \frac{w}{4}\sum_{t,t'}^{T} \gamma_{t,t'}(\alpha_t - \alpha_{t'})^T(\alpha_t - \alpha_{t'})$ The first term (=the loss of the PU task) in Expression 12 is expressed in Expression 13. The second term (=the loss of the PN task) in Expression 12 is expressed in Expression 14. A variable Nu in Expression 13 is the number of unlabeled data items in the DU data DPU. A variable $N_+$ in Expression 13 is the number of positive data items in the PU data DPU. A variable J in Expressions 13 and 14 is a vector in which all elements are 1.

$J_S^{\hat{P}U}(\alpha) = \frac{1}{4N_u}\alpha^T \Psi_U^T \Psi_U \alpha + \frac{1}{2N_u}J^T \Psi_U \alpha - \frac{\pi}{N_+}J^T \Psi_P \alpha$ [Expression 13]

$J_S^{\hat{P}N}(\alpha) = \frac{1}{4M}\alpha^T \Psi_P^T \Psi_P \alpha +$ [Expression 14]

$\frac{1}{4M}\alpha^T \Psi_N^T \Psi_N \alpha + \frac{1}{2M}J^T \Psi_N \alpha - \frac{1}{2M}J^T \Psi_P \alpha$ $\Psi_P$ in Expression 13 is a vector (matrix) expressed in Expression 15. $\Psi_U$ in Expression 13 is a vector (matrix) expressed in Expression 16. $\Psi_{P-}$ in Expression 14 is a vector (matrix) expressed in Expression 17. $\Psi_N$ in Expression 14 is a vector (matrix) expressed in Expression 18. A variable $M_+$ in Expression 17 is the number of positive data items in the PN data DPN. A variable $M_-$ in Expression 18 is the number of negative data items in the PN data DPN. A function $\Psi_1(x)$ in Expressions 15 to 18 is expressed in Expression 19. A variable O in Expression 19 is a vector in which all elements are 0.

$\Psi_P = (\psi_{t1}(x_1), \ldots, \psi_{tN_+}(x_{N_+}))^T \in R^{N_+ \times bT}$ [Expression 15]

$\Psi_U = (\psi_{t1}(x_1), \ldots, \psi_{tN_u}(x_{N_u}))^T \in R^{N_u \times bT}$ [Expression 16]

$$\Psi_P = (\psi_{t1}(x_1'), \ldots, \psi_{tM+}(x_{M+}'^+))^T \in R^{M+\times bT} \quad \text{[Expression 17]}$$

$$\Psi_N = (\psi_{t1}(x_1'), \ldots, \psi_{tM-}(x_{M-}'^-))^T \in R^{M-\times bT} \quad \text{[Expression 18]}$$

$$\psi_t(x) = ((O_{b(t-1)}{}^T, \varphi_t(x)^T, O_{b(T-t)}{}^T) \in R^{bT} \quad \text{[Expression 19]}$$

A coefficient parameter α for minimizing such a learning criterion is able to be calculated from a learning rule shown in Expression 20. A variable I in Expression 20 is a unit matrix. A variable C in Expression 20 is a matrix in which elements in t rows and t' columns are expressed in Expression 21.

$$\hat{\alpha} = \left(\frac{N}{L}\frac{1}{2N_u}\Psi_U^T\Psi_U + \frac{1}{2L}\Psi_P^T\Psi_P + \frac{1}{2L}\Psi_N^T\Psi_N + C\otimes I_b\right)^{-1} \quad \text{[Expression 20]}$$

$$\left(\frac{N}{L}\frac{\pi}{N_+}\Psi_P^TJ - \frac{N}{L}\frac{\pi}{2N_u}\Psi_U^TJ + \frac{1}{2L}\Psi_P^TJ - \frac{1}{2L}\Psi_N^TJ\right)$$

$$C_{t,t'} = \begin{cases} \lambda_t + w\sum_{t,t''=1}^{T}\gamma_{t,t''} - w\gamma_{t,t} & (t = t') \\ -w\gamma_{t,t'} & (t \neq t') \end{cases} \quad \text{[Expression 21]}$$

The state estimation unit 123 optimizes the coefficient parameter α based on the training rule. Here, the learning criterion includes the hyper parameters λ, w, and γ to be manually set. There is a possibility that the basis vector φ(x) will include the hyper parameters in some cases. Thus, in order to optimize the coefficient parameter α while setting the hyper parameter, the state estimation unit 123 may optimize the coefficient parameter α in the following order. Specifically, the state estimation unit 123 initially divides the training data items DP (that is, the PN data items DPN and the PU data items DPU) into first data items to be used to optimize the coefficient parameter α after candidates of the hyper parameter are set and second data items to be used to verify the coefficient parameter α optimized by using the first data items (to verify the precision of the degree of sleepiness estimated by using the coefficient parameter α optimized by using the first data items). For example, the state estimation unit 123 may use a predetermined percentage (for example, 80%) of data items among the training data items DP, as the first data items, and may use a remaining percentage (for example, 20%) of data items among the training data items DP, as the second data items. Subsequently, the state estimation unit 123 optimizes the coefficient parameter α by using the first data after predetermined candidate values are respectively set for the hyper parameters λ, w, and γ. Thereafter, the state estimation unit 123 verifies the optimized coefficient parameter α by using the second data. Specifically, the state estimation unit 123 obtains the output value of the linear model g(x) by inputting the feature value x included in the second data to the linear model g(x) specified by the coefficient parameter α optimized by using the first data. Subsequently, the state estimation unit 123 verifies the precision of the degree of sleepiness by comparing the output value of the linear model g(x) with the label data included in the second data. The state estimation unit 123 repeats such operations until the optimum hyper parameters λ, w, and γ are found. Thereafter, the coefficient parameter α is optimized by using the optimum hyper parameters λ, w, and γ and the training data items DP (that is, both the first data items and the second data items). As a result, the coefficient parameter α is optimized. The optimized coefficient parameter α is stored in the storage device 13.

When a degree of similarity between the tasks is previously known, the coefficient parameter may not be optimized by using the hyper parameter γ.

The processing from steps S211 to S25 described above is repeated. That is, as long as the driver drives the vehicle, new PU data DPU continues to be generated, and the coefficient parameter α continues to be optimized by using the newly generated PU data DPU in addition to the already generated PN data DPN and PU data DPU.

(3) Technical Effect

According to the state estimation system 1 described above, the content (that is, the coefficient parameter α) of the estimation operation is optimized by using the PN data DPN related to the detection result of the electrocardiogram of the subject different from the driver before the state estimation system 1 starts the estimation operation for estimating the degree of sleepiness of the driver. Thus, even though the state estimation system 1 starts the estimation operation in a state in which the training operation using the detection result of the electrocardiogram of the driver is not performed, the state estimation system 1 can estimate the degree of sleepiness of the driver with relatively high precision. Since the electrocardiogram of the driver as a target of which the degree of sleepiness is estimated by the state estimation system 1 may not be actually detected before the state estimation system 1 starts the estimation operation, the burden of the driver is reduced.

Meanwhile, as long as the PN data DPN is not data related to the detection result of the electrocardiogram of the driver, the content of the estimation operation optimized by using the PN data DPN (that is, the content of the estimation operation optimized without using the PU data) is not limited to be optimal for the driver due to the influence of individual differences. However, in the present embodiment, the content of the estimation operation is optimized by using the PU data DPU related to the detection result of the electrocardiogram of the driver after the state estimation system 1 starts the estimation operation. Thus, the state estimation system 1 can optimize the content of the estimation operation so as to correspond to the driver as a target of which the degree of sleepiness is estimated by the state estimation system 1 with consideration for the detection result of the electrocardiogram of the subject.

Figure 6:
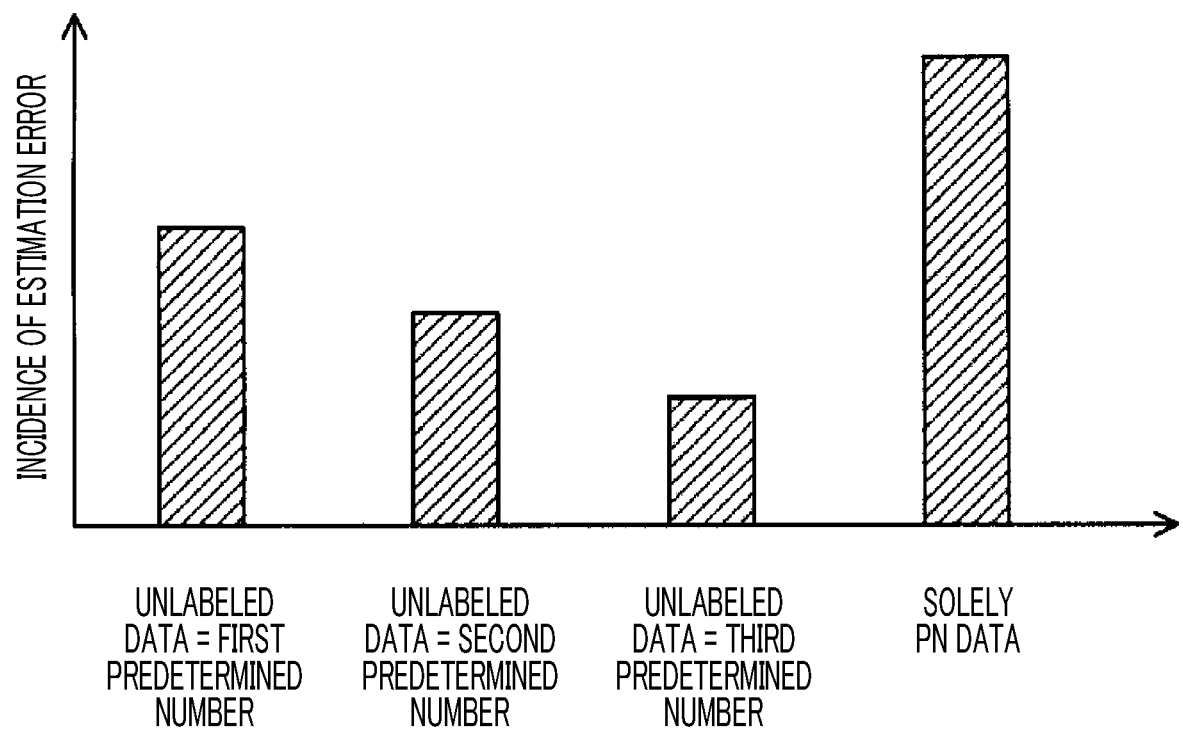
FIG. 6 is a graph showing an incidence of an estimation error.

As a result, the state estimation system 1 can appropriately estimate the degree of sleepiness of the driver. For example, FIG. 6 is a graph showing an incidence of an estimation error of the degree of sleepiness when the coefficient parameter α is optimized by using the PU data DPU including a first predetermined number of unlabeled data items (that is, feature values which are not associated with the label data), an incidence of an estimation error of the degree of sleepiness when the coefficient parameter α is optimized by using the PU data DPU including a second predetermined number (here, the second predetermined number is larger than the first predetermined number) of unlabeled data items, an incidence of an estimation error of the degree of sleepiness when the coefficient parameter α is optimized by using the PU data DPU including a third predetermined number (here, the third predetermined number is larger than the second predetermined number) of unlabeled data items, and an incidence of an estimation error of the degree of sleepiness when the coefficient parameter α is optimized without using the PU data DPU (that is, by using solely the PN data DPN). As shown in FIG. 6, the incidence of the estimation error is further decreased when the coefficient parameter α is optimized by using both the PN data DPN and the PU data DPU than that when the coefficient parameter α is optimized by using solely the PN data DPN. The larger the number of unlabeled data items (that is, the longer a time for the driver drives the vehicle or a time for the driver wears the electrocardiogram sensor 11), the lower the incidence of the estimation error.

(4) Modification Example

It has been described above that the update criterion to be satisfied in order to start the optimization of the coefficient parameter α using the PU data DPU and the PN data DPN includes a condition related to the data amount of PU data items DPU newly generated after the previous coefficient parameter α is optimized. However, the update criterion may include another condition in addition to or instead of the condition related to the data amount of the PU data items DPU. For example, the update criterion may include a condition related to the number of times the driver rides the vehicle (for example, a condition in which the number of times the driver rides the vehicle after the previous coefficient parameter α is optimized is equal to or larger than a predetermined number of times). For example, the update criterion may include a condition related to a time for which the driver rides the vehicle (for example, a condition in which a time for which the driver rides the vehicle after the previous coefficient parameter α is optimized is equal to or longer than a predetermined time). For example, the update criterion may include a condition related to a request from the driver (for example, a condition in which the driver requests the optimization of the coefficient parameter α). Alternatively, the state estimation unit 123 may optimize the coefficient parameter α whenever the PU data DPU is obtained without using the update criterion. That is, the state estimation unit 123 may perform online learning using the PN data DPN and the PU data DPU.

In a specific method of optimizing the coefficient parameter α using the PU data DPU and the PN data DPN, the learning criterion when the squared loss ls(m) is adopted is set. However, a different learning criterion may be set when a loss (for example, a double hinge loss, an exponential loss, or a logistic loss) different from the squared loss ls(m) is adopted. When the double hinge loss or the logistic loss is adopted, since it is difficult to optimize the coefficient parameter α by using an analysis method as in a case where the squared loss ls(m) is adopted, the coefficient parameter α may be optimized by using a method such as a convex optimization method.

The specific method of the optimization of the coefficient parameter α using the PU data DPU and the PN data DPN is merely an example. Thus, the state estimation unit 123 is not limited to the aforementioned method, and the coefficient parameter α may be optimized by any method as long as the coefficient parameter α can be optimized by using the PN data DPN and the PU data DPU. For example, the state estimation unit 123 may optimize the coefficient parameter α by any method as long as the coefficient parameter α can be optimized such that (i) an error between the output value output from the linear model g(x) when the feature value x included in the PN data DPN is input to the linear model g(x) expressed in Expression 4 described above and the label data included in the PN data DPN is minimized or is equal to or smaller than a first allowable value, (ii) an error between the output value output from the linear model g(x) when the feature value x associated with the label data among the PU data items DPU is input to the linear model g(x) expressed in Expression 4 described above and the label data included in the PU data DPU is minimized or is equal to or smaller than a second allowable value, and (iii) the feature value x included in the PU data DPU can be appropriately classified into two different classes (that is, the sleepy state and the unsleepy state).

It has been described above that the state estimation system 1 estimates the degree of sleepiness of the driver based on the electrocardiogram of the driver. However, the state estimation system 1 may estimate the degree of sleepiness of the driver based on another biological information of the driver in addition to or instead of the electrocardiogram of the driver. For example, the state estimation system 1 may capture an image of the driver by using a camera, may perform image processing on the captured image, may extract a feature value (for example, a feature value related to at least one of the facial expression and action of the driver) of the image, and may estimate the degree of sleepiness of the driver based on the extracted feature value.

It has been described above that the state estimation system 1 estimates the degree of sleepiness of the driver based on the biological information of the driver. However, the state estimation system 1 may estimate any state of the driver based on the biological information of the driver. For example, the state estimation system 1 may extract a feature value (for example, a feature value related to the content ratio of theta waves) related to a brain wave of the prefrontal cortex of the driver from the biological information of the driver, and may estimate a degree of concentration (conversely, a degree of relaxation) of the driver on the driving based on the extracted feature value. In this case, the state estimation system 1 may obtain the biological information after the driver relaxes for a predetermined time or longer, and may generate data obtained by associating the feature value of the obtained biological information with the label data indicating the label representing that the state of the subject relaxes, as data corresponding to the PU data DPU. The state estimation system 1 may obtain the biological information of the subject after the subject performs a specific work (for example, at least one of document preparation, reading, and video watching), and may generate data obtained by associating the feature value of the obtained biological information with the label data indicating the actual state of the subject, as data corresponding to the PN data DPN.

It has been described above that the state estimation system 1 estimates the state of the driver based on the biological information of the driver. However, the present embodiment is not limited to the case where the state estimation system estimates the state of the driver, and the state estimation system 1 may estimate a state of any user based on the biological information of the any user. It has been described above that the state estimation system 1 estimates the state of the user based on the electrocardiogram or the captured image (that is, based on the biological information of the user). However, the state estimation system 1 may estimate a state of any user based on any behavior information (that is, information related to the behavior of the user) of any user in addition to or instead of the biological information. For example, the state estimation system 1 may estimate the state of any user by using the behavior information of the user obtained from an acceleration sensor or an angular velocity sensor attached to the arm and trunk.

The aforementioned embodiment is summarized as follows.

A state estimation system according to the present embodiment includes a processor configured to: obtain first input data related to at least one of biological information and behavior information of a first user; obtain second input data related to at least one of biological information and behavior information of a second user different from the first user; perform an estimation operation for estimating a state of the first user based on the first input data; perform a training operation for optimizing a content of the estimation operation by using i) first training data which includes the first input data and first label data indicating a state of the first user corresponding to the first input data so as to associate the first input data and the first label data with each other, ii) second training data which includes the first input data so as not to associate the first input data and the first label data with each other, and iii) third training data which includes the second input data and second label data indicating a state of the second user corresponding to the second input data so as to associate the second input data and the second label data with each other; and output a signal indicating information related to the content of the estimation operation.

According to the above state estimation system, the content of the estimation operation is optimized by using both the data (that is, the second and third input data) related to at least one of the biological information and the behavior information of the first user and the data (that is, the fourth input data) related to at least one of the biological information and the behavior information of the second user. Thus, the content of the estimation operation is optimized to some extent based on at least one of the biological information and the behavior information of the second user different from the first user before the state estimation system starts to estimate the state of the first user. The content of the estimation operation is further optimized based on at least one of the biological information and the behavior information of both the first user and the second user after the state estimation system starts to estimate the state of the first user. Thus, the content of the estimation operation is optimized while reflecting the influence of the individual differences of the biological information. Therefore, the state estimation system according to the present embodiment can appropriately estimate the state of the first user based on at least one of the biological information and the behavior information of the first user.

In the above state estimation system, the training operation may include a multi-task training operation for performing a first processing task and a second processing task based on a multi-task learning method, the first processing task being a processing task for optimizing the content of the estimation operation by using the first leaning data and the second training data, and the second processing task being a processing task for optimizing the content of the estimation operation by using the third training data.

According to the above state estimation system, the content of the estimation operation is more appropriately and more efficiently optimized by performing the multi-task learning operation.

In the above state estimation system, the first processing task may be a processing task based on a positive unlabeled (PU) training method, and the second processing task is a processing task based on a supervised training method.

Since the first processing task is the task performed by using the first training data including the first label data and the second training data without including the second label data, it is desirable that the first processing task is performed based on the PU training method, but not particularly limited thereto. Meanwhile, since the second processing task is the task performed by using the third training data including the third label data, it is desirable that the second processing task based on the supervised training method, but not particularly limited thereto. Thus, according to the above state estimation system, the content of the estimation operation is more appropriately and more efficiently optimized by performing the first processing task based on the PU training method and the second processing task based on the supervised learning method based on the multi-task learning method.

In the above state estimation system, the processor may be configured to estimate which the state of the first user is a first state or a second state different from the first state; and the first training data may include the first input data detected when the state of the first user is the first state and the first label data indicating that the state of the first user is the first state so as to associate the second input data and the first label data with each other.

According to the above state estimation system, the content of the estimation operation for classifying the state of the user into two classes is appropriately optimized.

In the above state estimation system, the processor is configured to perform the training operation by using a plurality of third training data items which respectively corresponds to a plurality of second users.

According to the above state estimation system, the content of the estimation operation is optimized by using the third training data (that is, the fourth input data items related to at least one of the biological information and the behavior information of the second users) corresponding to the second users. Thus, the content of the estimation operation is optimized while further reflecting the influence of the individual differences of at least one of the biological information and the behavior information. Therefore, the state estimation system according to the present embodiment can more appropriately estimate the state of the first user based on at least one of the biological information and the behavior information of the first user.

In the above state estimation system, the first user may be a driver of a vehicle, and the state of the first user may be a degree of sleepiness of the first user.

According to the above state estimation system, the degree of sleepiness of the driver can be appropriately estimated based on at least one of the biological information and the behavior information of the driver.

In the above state estimation system, the first input data included in the first training data may be detected until a predetermined time elapses since the first user starts to drive the vehicle; and the first label data may be data indicating that the first user is unsleepy.

It can be seen through the present test that there is a relatively high possibility that the first user will be unsleepy until the predetermined time elapses since the first user starts to drive the vehicle (immediately after the first user starts to drive the vehicle). Thus, according to the above state estimation system, the first training data can be appropriately obtained.

In the above state estimation system, the first input data included in the second training data may be detected after a predetermined time elapses since the first user starts to drive the vehicle.

The degree of sleepiness of the first user is changed due to the influence of various causes after the predetermined time elapses since the first user starts to drive the vehicle. That is, the first user may be unsleepy or may be sleepy. Even in this case, according to the above state estimation system, the data related to at least one of the biological information and the behavior information detected after the predetermined time elapses since the first user starts to drive the vehicle is obtained as the second training data including the third input data which is not associated with the second label data. Thus, the training operation is performed by using a larger amount of training data items than that when the third input data related to at least one of the biological information and the behavior information detected after the predetermined time elapses since the first user starts to drive the vehicle is not used in the training operation. As a result, the content of the estimation operation is more appropriately and rapidly optimized.

The disclosure is not limited to the aforementioned embodiment, and may be appropriately modified without departing from the gist or ideal of the disclosure to be read from the claims and the entire specification. A state estimation system according to a modification example is included in the technical scope of the disclosure.

What is claimed is:

1. A state estimation system comprising a processor configured to:
    obtain first input data related to at least one of biological information and behavior information of a first user;
    obtain second input data related to at least one of biological information and behavior information of a second user different from the first user;
    perform an estimation operation for estimating a state of the first user based on the first input data;
    perform a training operation for optimizing a content of the estimation operation by using i) first training data which includes the first input data and first label data indicating a state of the first user corresponding to the first input data so as to associate the first input data and the first label data with each other, ii) second training data which includes the first input data so as not to associate the first input data and the first label data with each other, and iii) third training data which includes the second input data and second label data indicating a state of the second user corresponding to the second input data so as to associate the second input data and the second label data with each other; and
    output a signal indicating information related to the content of the estimation operation.

2. The state estimation system according to claim 1, wherein the training operation includes a multi-task learning operation for performing a first processing task and a second processing task based on a multi-task learning method, the first processing task being a processing task for optimizing the content of the estimation operation by using the first leaning data and the second training data, and the second processing task being a processing task for optimizing the content of the estimation operation by using the third training data.

3. The state estimation system according to claim 2, wherein:
    the first processing task is a processing task based on a positive unlabeled learning method; and
    the second processing task is a processing task based on a supervised learning method.

4. The state estimation system according to claim 1, wherein:
    the processor is configured to estimate which the state of the first user is a first state or a second state different from the first state; and
    the first training data includes the first input data detected when the state of the first user is the first state and the first label data indicating that the state of the first user is the first state so as to associate the second input data and the first label data with each other.

5. The state estimation system according to claim 1, wherein the processor is configured to perform the training operation by using a plurality of third training data items which respectively corresponds to a plurality of second users.

6. The state estimation system according to claim 1, wherein:
    the first user is a driver of a vehicle; and
    the state of the first user is a degree of sleepiness of the first user.

7. The state estimation system according to claim 6, wherein:
    the first input data included in the first training data is detected until a predetermined time elapses since the first user starts to drive the vehicle; and
    the first label data is data indicating that the first user is unsleepy.

8. The state estimation system according to claim 6, wherein the first input data included in the second training data is detected after a predetermined time elapses since the first user starts to drive the vehicle.

* * * * *

UNITED STATES PATENT AND TRADEMARK OFFICE
CERTIFICATE OF CORRECTION

PATENT NO. : 10,556,595 B2
APPLICATION NO. : 16/162813
DATED : February 11, 2020
INVENTOR(S) : Hirotaka Kaji and Masashi Sugiyama It is certified that error appears in the above-identified patent and that said Letters Patent is hereby corrected as shown below:

In the Specification

Column 11, Line 18, after "coefficient parameters", delete "a" and insert --$\alpha$--, therefor.

Column 11, Line 20, after "coefficient parameters", delete "a" and insert --$\alpha$--, therefor.

Column 11, Line 23, after "coefficient parameters", delete "a" and insert --$\alpha$--, therefor.

Column 11, Line 25, after "coefficient parameters", delete "a" and insert --$\alpha$--, therefor.

Column 11, Line 27, after "coefficient parameters", delete "a" and insert --$\alpha$--, therefor.

Column 11, Line 29, after "coefficient parameters", delete "a" and insert --$\alpha$--, therefor.

Column 11, Line 32, after "coefficient parameters", delete "a" and insert --$\alpha$--, therefor.

Column 11, Line 34, after "coefficient parameters", delete "a" and insert --$\alpha$--, therefor.

Signed and Sealed this
Seventh Day of April, 2020

Andrei Iancu
*Director of the United States Patent and Trademark Office*